United States Patent
Silva et al.

(10) Patent No.: US 10,026,508 B2
(45) Date of Patent: Jul. 17, 2018

(54) GEOGRAPHIC UTILIZATION OF ARTIFICIAL INTELLIGENCE IN REAL-TIME FOR DISEASE IDENTIFICATION AND ALERT NOTIFICATION

(71) Applicant: Guardian Health Technologies, LLC, Chicago, IL (US)

(72) Inventors: Julio Cesar Silva, Naperville, IL (US); Dino Peter Rumoro, Winfield, IL (US)

(73) Assignee: Guardian Health Technologies, LLC, Chicago, IL (US)

( * ) Notice: Subject to any disclaimer, the term of this patent is extended or adjusted under 35 U.S.C. 154(b) by 0 days.

(21) Appl. No.: 15/387,506

(22) Filed: Dec. 21, 2016

(65) Prior Publication Data

US 2017/0169182 A1 Jun. 15, 2017

Related U.S. Application Data

(63) Continuation of application No. 14/768,304, filed as application No. PCT/US2014/027139 on Mar. 14, 2014, now Pat. No. 9,594,878.

(Continued)

(51) Int. Cl.
*G16H 50/70* (2018.01)
*G06F 19/00* (2018.01)
*G16H 10/60* (2018.01)

(52) U.S. Cl.
CPC ........... *G16H 50/70* (2018.01); *G06F 19/322* (2013.01); *G06F 19/3443* (2013.01); *G16H 10/60* (2018.01)

(58) Field of Classification Search
None
See application file for complete search history.

(56) References Cited

U.S. PATENT DOCUMENTS 6,551,243 B2 * 4/2003 Bocionek ............... A61B 5/411
 128/923
8,392,152 B2 * 3/2013 Rao ..................... G06F 19/3493
 600/300

(Continued)

FOREIGN PATENT DOCUMENTS

WO WO00/41613 A2 7/2000

OTHER PUBLICATIONS

Carneiro et al., Google Trends: A Web-Based Tool for Real-Time Surveillance of Disease Outbreaks, Nov. 15, 2009, Surfing the Web, CID, pp. 1557-1564.*

(Continued)

*Primary Examiner* — Alan Chen
(74) *Attorney, Agent, or Firm* — Brinks Gilson & Lione

(57) ABSTRACT

Systems and methods for generating a diagnosis are provided. In some aspects, a computing device receives medical information for a patient, wherein each medical information item in the medical information comprises a date, a source, and a medical state. The computing device constructs, in a memory of the computing device, a diagnosis tree for the patient, wherein the diagnosis tree comprises a patient node, the patient node having first children nodes corresponding to the dates or the sources, and the first children nodes having second children nodes corresponding to the medical states. The computing device generates a diagnosis for the patient using the constructed diagnosis tree.

17 Claims, 10 Drawing Sheets

Related U.S. Application Data

(60) Provisional application No. 61/794,393, filed on Mar. 15, 2013.

(56) References Cited

U.S. PATENT DOCUMENTS

| | | |
|---|---|---|
| 2006/0036619 A1* | 2/2006 | Fuerst ................ G06F 19/3443 |
| 2009/0062623 A1 | 3/2009 | Cohen et al. |
| 2010/0070300 A1 | 3/2010 | Anderson et al. |
| 2010/0088320 A1 | 4/2010 | Fortier et al. |
| 2013/0044925 A1 | 2/2013 | Kozuka et al. |
| 2014/0025393 A1 | 1/2014 | Wang et al. |

OTHER PUBLICATIONS

Clifton et al., Privacy Preserving Data Integration and Sharing, Jun. 13, 2004, DMKD '04, pp. 19-26.*
Tsui et al., Technical Description of RODS: A Real-time Public Health Surveillance System, Sep./Oct. 2003, Journal of the American Medical Informatics Association, vol. 10 No. 5, pp. 399-408.*
International Search Report dated Oct. 31, 2014 from corresponding PCT Application No. PCT/US2014/27139.

* cited by examiner

GEOGRAPHIC UTILIZATION OF ARTIFICIAL INTELLIGENCE IN REAL-TIME FOR DISEASE IDENTIFICATION AND ALERT NOTIFICATION

CROSS REFERENCE TO RELATED APPLICATION

This application is a continuation of U.S. application Ser. No. 14/768,304, filed Aug. 17, 2015, which is the U.S. National Stage of International Application No. PCT/US2014/027139, filed Mar. 14, 2014, published in English, and claims the benefit of U.S. Provisional Application No. 61/794,393, filed Mar. 15, 2013, and entitled, "GEOGRAPHIC UTILIZATION OF ARTIFICIAL INTELLIGENCE IN REAL-TIME FOR DISEASE IDENTIFICATION AND ALERT NOTIFICATION," the entire disclosure of which is incorporated herein by reference.

GOVERNMENT LICENSE RIGHTS

This invention was made with government support under contracts numbers W81XWH-05-1-0614, W81XWH-06-1-0785, W81XWH-09-1-0662, AND W81XWH-11-1-0711, awarded by the United States Army Medical Research Acquisition Activity. The Government has certain rights to this invention.

BACKGROUND

The subject technology is generally directed to computer-implemented disease identification and detection of outbreaks of diseases.

A medical professional responsible for diagnosing a patient may be hesitant to diagnose the patient with an uncommon condition, for example, due to his/her own unfamiliarity with the condition or due to his/her own inability to believe that the condition is occurring. Also, the medical professional may be unfamiliar with other recent diagnoses in his/her geographic area. As a result, an outbreak of a rare medical condition in a geographic area (e.g., polio in the Chicago metropolitan area) may be difficult to detect or may not be detected until the condition becomes very widespread. As the foregoing illustrates a new approach for disease identification and detection of outbreaks of diseases may be desirable.

SUMMARY

Methods, computer-readable media, and systems for generating a diagnosis are provided. In some aspects, a computing device receives medical information for a patient, wherein each medical information item in the medical information comprises a date, a source, and a medical state. The computing device constructs, in a memory of the computing device, a diagnosis tree for the patient, wherein the diagnosis tree comprises a patient node, the patient node having first children nodes corresponding to the dates or the sources, and the first children nodes having second children nodes corresponding to the medical states. The computing device generates a diagnosis for the patient using the constructed diagnosis tree.

Methods, computer-readable media, and systems for detecting an outbreak of a medical condition are provided. In some aspects, a computing device receives reports of patients having a set of medical states, each report being associated with a same geographic area. The computing device determines, based on data stored in a medical data repository, that the set of medical states is associated with a specified condition. The computing device determines an outbreak of the specified condition in the geographic area based on the reports of the patients having the set of medical states. The computing device provides an indication of the outbreak of the specified condition in the geographic area.

It is understood that other configurations of the subject technology will become readily apparent from the following detailed description, where various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Features of the subject technology are set forth in the appended claims. However, for purpose of explanation, several aspects of the disclosed subject matter are set forth in the following figures.

DETAILED DESCRIPTION

Figure 1:
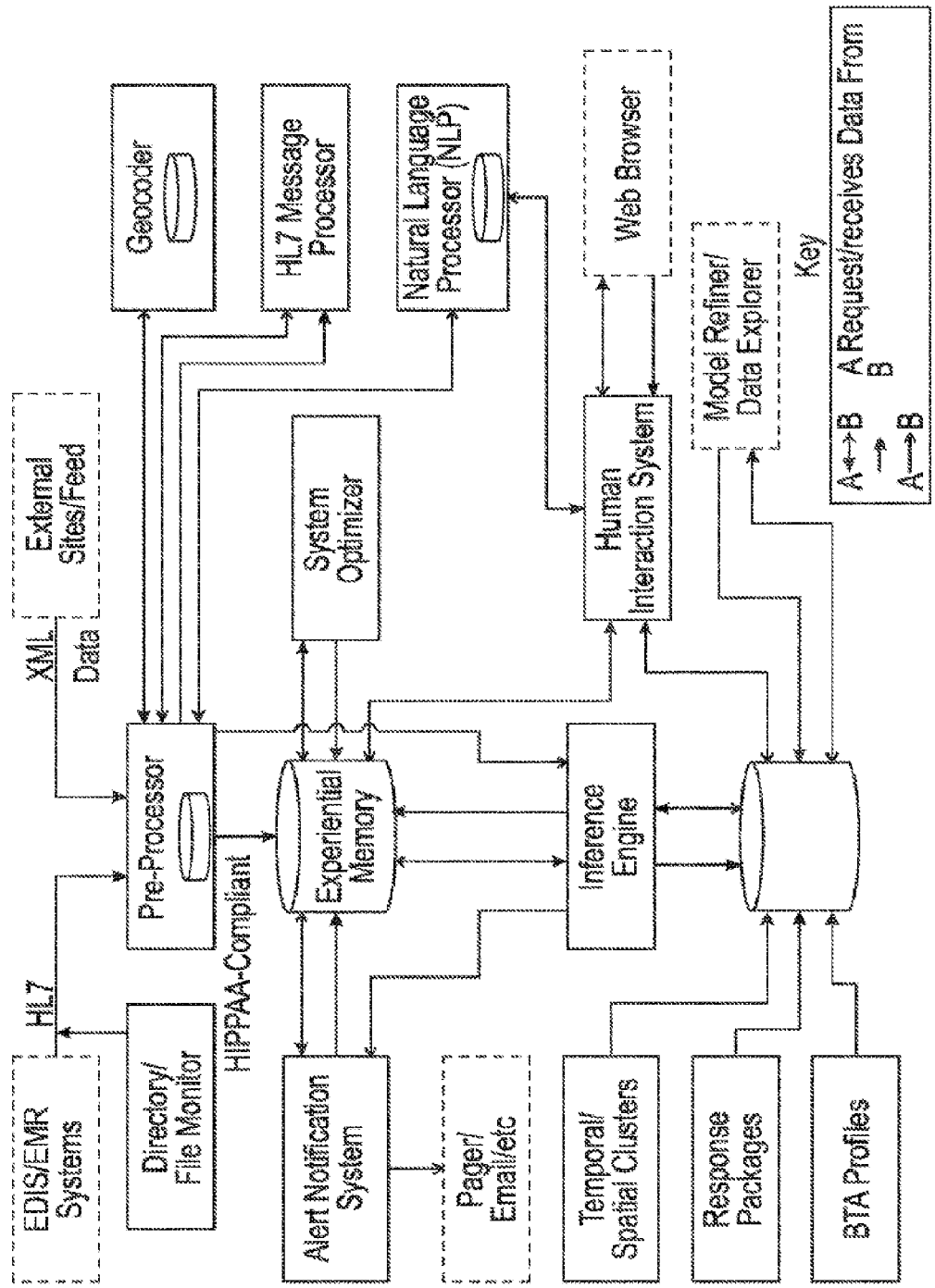
FIG. 1 illustrates an example system in which examples of the subject technology may be implemented.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent that the subject technology is not limited to the specific details set forth herein and may be practiced without these specific details. In some instances, certain structures and components are shown in block diagram form in order to avoid obscuring the concepts of the subject technology.

Real-time disease surveillance may be important for early detection of emerging infectious and non-infectious diseases, naturally occurring illnesses or the covert release of a biological threat agent. Some trend analysis systems collect data and categorize discreet clinical variables into syndrome cohorts. In some cases, analysis occurs days to weeks after the actual collection of the data. This inherent delay in analysis may, in some cases, preclude an efficient response to an emerging health threat. The subject technology may, in some cases, implement predictive analytics for operational efficiencies. For example, some of the techniques described herein may be used, among other things, to assimilate relevant data from multiple clinical sources to determine if a defined set of criteria are met for a patient's condition. The data may be used to determine a probability that the patient will be admitted to a hospital, develop a certain other condition, require a certain treatment, etc. Computing device(s) implementing the subject technology may also recommend certain treatments (e.g. to prescribe a first medication or not to prescribe a second medication) based on the assimilated data.

The subject technology can be implemented as a computer-implemented method, a computer system, or a non-transitory computer-readable medium including instruction (e.g., software code). The subject technology can be implemented on one or more computing devices. A computing device can include a server, a data repository, a database, a laptop computer, a desktop computer, a netbook, a mobile phone, a tablet computer, a personal digital music player, a personal digital assistant (PDA), etc.

The subject technology, in some implementations, relates to a real-time, scalable, automated, knowledge-based disease detection and diagnosis system. The subject technology, in some implementations, includes conducting real-time (e.g., immediate, within one minute, within ten minutes, within one hour, etc., or without any intentional delay) analysis of multiple pre-diagnostic parameters received from electronic medical records as they are routinely documented as part of a clinical encounter. Some implementations of the subject technology can be utilized at any location where a patient seeks treatment (e.g., emergency departments, doctors' offices, clinics, etc.). The data being analyzed in some implementations of the subject technology may include, among other things, chief complaints, history and physical examination notes, nursing and physician notes, other provider notes, radiology dictated reports or laboratory test results. The subject technology, according to some implementations, is able to analyze discreet variables from "check boxes" as well as "pull down" menus and has a robust natural language processor, based on the national library of medicine, to analyze free-text entries including comments of negation.

As used herein, the term "real-time" encompasses its plain and ordinary meaning including, but not limited to occurring without any intentional delay after an entry of a command or a triggering occurrence. For example, a command that is executed in real-time after a mouse click can be executed without any intentional delay after the mouse click, for example, within one second, ten seconds, one minute, ten minutes, one hour, etc. of the mouse click.

Some implementations of the subject technology include analyzing module(s). The analyzing module(s) can, in some cases, have one or both of two types: 1) pre-defined common disease definitions, for example, as provided by an expert authority, locally, regionally, nationally or world-wide (e.g., influenza-like illness as defined by the Centers for Disease Control (CDC) or locally occurring diseases as defined by public health or emergency management experts) and, 2) disease profiling for rarely occurring illnesses such as Anthrax or Smallpox. The analyzing module(s) can include artificial intelligence based module(s).

In some examples, the pre-defined definition module(s) can use a case definition for a certain medical condition as described, for example, by a higher authority content expert. One example of the certain medical condition is influenza-like illness (ILI) which is defined by the Centers for Disease Control (CDC). This information is programmed into computing device(s) implementing the subject technology and, as the computing device(s) receive data from the various modules of the patient electronic health record (EHR), the received data can be analyzed and converted into clinically useful information. The computing device(s) calculate a probability (expressed, for example, as a percent) of the patient having a given condition (e.g., as programmed into the computing device(s)) and provides this information to the user. If the patient has a high probability for a given disease entity, the user can initiate an appropriate intervention. The intervention may be, for example, an infection control process such as wearing a mask or even a clinical intervention such as antibiotic dispensation or vaccination.

As cumulative data is acquired from multiple patients, the computing device(s) can be programmed to provide a 7-day (or any other time period, including a fixed time period or a variable time period) rolling statistical averaging analysis to create thresholds. During periods of no disease activity, these thresholds can become the "normal" level of disease activity in the community. The community can be defined based on age, gender, physical characteristic(s), geographic location, etc. For example, the community can include American adults ages 18-65 or women over age 70 residing within 50 miles of Chicago, Ill. When disease activity occurs, this threshold may be breached, providing an indication (e.g., a first indication) of an outbreak. Early recognition of a specific disease outbreak can lead to early public health interventions on a widespread scale. The automaticity and real-time analysis that the subject technology provides translates into disease recognition far earlier than some other approaches, which may rely on human intervention of data submission, analysis, recognition, disseminated reporting, and/or intervention.

In some implementations, the information can be relayed to predetermined parties through one or more of several different approaches: pager; automated reports and graphs for any time period(s) requested (e.g., hourly, daily, weekly, monthly, etc); a user interface through a webpage, a mobile phone application, a tablet computer application, etc. The purpose for the various communication methods is to assure appropriate communication for various purposes for which the subject technology may be used. The various purposes may include one or more of reporting (e.g., mandatory reporting), clinical intervention, or public health oversight of community-based disease activity. The subject technology, in some implementations, is also able to geographically map a geographic location of where specific case(s) have emerged. The geographically mapped information or geographic location information could help public health or emergency response officials quickly contain an outbreak.

In some examples, the subject technology can be used to provide the details set forth above for other clinical situations that may arise in a community or even from specific mass gatherings, for example, febrile rash illness, localized cutaneous lesions, acute febrile respiratory illness, gastrointestinal illness, botulism-like illness, hemorrhagic-illness, unexplained deaths or severe illness and poison or toxin exposure, or environmental heat illness. In these cases, the subject technology can follow case definition if provided. If the case definition is not provided, the subject technology can include analyzing various International Statistical Classification of Diseases and Related Health Problems (ICD, for example, ICD-9) codes for clinical diagnosis. In some examples, the subject technology does not rely solely on final diagnosis and ICD-9 codes. Instead, the subject technology can include analyzing entire or partial contents of the medical record with the understanding that a clinician may provide an inaccurate ICD-9 code which could lead to a misdiagnosis if the inaccurate ICD-9 code were the sole factor in determining the presence of a disease entity. According to some examples, the unbiased, automated, artificial-intelligence based data analysis of the subject technology can eliminate the potential of a clinician drawing the wrong conclusion from the data provided during a clinical encounter. In addition, the subject technology can account for all or some aspects of the encounter which may not be readily apparent to an individual health care provider, as patients sometimes may relay their symptoms in piece-meal.

In contrast to the pre-defined illness programming, disease profiling for rarely occurring illnesses can be a more elaborate process that takes disease surveillance for rarely occurring illnesses beyond simple trend analysis. Some of the subject technology can be used to elevate the artificial intelligence technique(s) described above for use by a clinician prepared to recognize unfamiliar disease(s). The subject technology, in some implementations, can be used to recognize the occurrence of Category-A, Biological Threat Agents (BTAs): Anthrax, Botulism, Hemorrhagic Fever, Pneumonic Plague, Smallpox and Tularemia. The subject technology, in some implementations, can be used to recognize the occurrence of Category-B, BTAs: Pandemic Influenza, SARS, Q fever, Ricin, Brucellosis, food safety threats, West Nile virus, water safety threats, Typhus and Glanders. The subject technology, in some implementations, can be used to recognize chemical agents, for example, Chemical Threat Agents: nerve gas, blistering agents, choking agents and asphyxiates. The subject technology, in some implementations, can be used to recognize radiological exposures.

The infrequent presentation of rarely occurring illnesses can benefit by using a different artificial intelligence knowledge-base, as described herein. In these cases, the literature can be manually searched, by clinical expert(s), for the historic cases describing the actual disease process. Information can be manually garnered, by clinical expert(s), from those literature searches and tabulated in cumulative form. Weighted factors of strength can be applied to signs, symptoms, and diagnostic studies as a disease profile or "fingerprint" is formed. This information can be programmed into computing device(s) implementing examples of the subject technology and the profile can be run against actual patient encounters in which the disease was not present in order to refine the profile by studying the cause of false positive alerts. Once refined, the subject technology can be used to run the profile against known cases of the disease, for example, from the literature that were not used in the original profile development. If too few positive cases are present in the literature, a synthetic patient can be generated. Again, results of false negatives can be studied to further refine the final disease "fingerprint" formed as described herein.

The subject technology, in some implementations, can analyze all or some data sources for all or some patients to determine the percent probability of the presence of a specific disease. For these rarely occurring illnesses, community based thresholds, in some cases, may not exist. Thus, a positive result above a predetermined percent probability can be considered significant. Once significance is established, a warning, for example, in the form of a webpage, a printed page, an electronic (e.g., email) message or a message to a mobile device (e.g., a short messaging service (SMS) message or an alert pushed to the mobile device) can be sent to designated individuals. The subject technology, in some cases, has a user interface that can also be used to monitor real-time analysis of patient populations for rarely occurring disease attributes.

The subject technology, in some implementations, relates to a powerful and highly flexible artificial intelligence framework that rapidly compares ED patient symptoms to a library of disease profiles. The profiles can be useful for at least two reasons. First, these profiles can allow the encapsulation of expert medical knowledge and case summaries in a format that may be useful for rapid categorization tasks. Second, these profiles allow knowledge to be applied at facilities that do not have access to the subject matter experts from which the knowledge was extracted.

In addition to the artificial intelligence-based Inference Engine component and the disease profiles, the subject technology, in some examples, can include a Pre-Processor, an Alert Notification System, a Human Interaction System, an Automated Knowledge Acquisition System, a set of Response Packages and a set of relational databases managed by a Database Management System (DBMS). FIG. 1 provides an overview of a system in which some examples of the subject technology can be implemented.

The pre-processor, in some examples, includes three major parts. The first part is a Transmission Control Protocol (TCP) server that listens on one or more specific ports for incoming messages (e.g., Health Level 7 (HL7) messages). The second part is a message processor. The message processor converts all of the information from the incoming messages into an internal format and manages any links between different messages (e.g., multiple messages for the same patient, a lab order and its associated results, a very large message broken into multiple smaller messages, etc). The message processor also removes all individually-identifying information from the incoming messages in order to maintain Health Insurance Portability and Accountability Act (HIPAA) compliance. Any pieces of information that could be used to identify a patient (e.g., SSN, name, MRN) are removed from the incoming data and stored in a separate area in the DBMS that is accessible only to specifically authorized users. Also, all patient address information is obfuscated by first converting the address to a latitude and longitude coordinate, and then rounding those coordinates to the nearest 100 meters (or other radius).

One other part of the pre-processor, in some examples, is the Natural Language Processing (NLP) sub-system. The NLP subsystem component mines through all or some incoming free-text for words or phrases that are associated with one or more of the known disease profiles. As a result, the text becomes more useful to the inference engine and irrelevant information may be removed. Also HIPAA compliance is maintained with free-text data as well as it is with structured data.

In some implementations, the pre-processor may be implemented with component parts different from those specified above.

In some examples, the alert notification system is triggered when the inference engine generates an alert. Alerts can be triggered either by an individual case having a high probability of a particular diagnosis, or by a group of similar cases—clustered in time and in space—having a probability above a separate, and possibly lower, BTA-specific threshold. The alert notification system broadcasts these alerts to the appropriate people and resends unanswered alerts periodically. The human interaction system can be a web-based user interface or another user interface. The interface supports monitoring and interactive exploration of stored data and provides a mechanism for users to respond to alerts generated by the system.

In some examples, the automated knowledge-acquisition system uses self-learning methods to improve the BTA and non-BTA detection capabilities described herein. This automated learning system can, in some examples, perform four major functions. First, the automated learning system determines the missing or new information that, if known, would be most effective in more accurately classifying "borderline" cases. The automatic learning system obtains the information either by reviewing older archived data or through an efficient interaction with expert users. Second, the automated learning system examines the current models contained in the knowledge base and refines the structure and parameters of these models in order to optimize the accuracy and efficiency of the evaluation process. Third, the automated learning system reviews all of the stored data, both current and archived, in order to discover patterns that may suggest the occurrence of a disease that is currently unknown to the computing device(s) implementing the subject technology. Fourth, the automated learning system handles knowledge-base portability when the subject technology is used to transfer clinical knowledge between different medical facilities. In some examples, the automated learning system can have other functionality or can lack one or more of the functionalities described above.

The response packages managed by the subject technology, in some cases, contain information about each known disease or some of the known diseases in a human-readable format. The information can include differential diagnoses, clinical procedures and isolation protocols. The response packages can be made available through the user interface in the event of an alert being triggered.

The subject technology can be designed to perform under conditions of increased volume without significant impact to system performance. Scalability of some examples of the subject technology can be important for at least two primary reasons. First, the surveillance of populous areas can require systems to operate at disparate levels of patient volume. Second, in the event of an incident, the volume of patient transactions may exceed normal levels of operation. In some cases, the subject technology is able to adapt to these potential changes. In some case, the subject technology can be implemented as a multi-threaded application with a robust TCP server and Database Management System (DBMS) to handle a wide variety of load levels.

To support heavy user connection levels, the user interface can be implemented, using Adobe Systems' Flex technology or similar technologies. This technology allows each computer that connects to the computing device(s) implementing the subject technology to handle its own caching and rendering. Thus, the subject technology can provide a very rich cross-platform web-based application to each user without placing a heavy processing demand on the server. As a result, the subject technology can operate during times of highly concurrent access, for example, during a disease outbreak.

In some examples, clinical profiles can be developed for the Category A and Category B BTAs as well as for more common infectious diseases such as influenza, gastroenteritis and the common cold. The clinical profiles can be used to create the disease models and to determine the thresholds that the inference engine uses to determine whether or not new data generates an alert. The inference engine can use these disease models to classify patient visits according to the likelihood that each visit is the result of exposure to a known BTA.

The subject technology, in some implementations, effectively balances the dual challenges of early detection of individual non-infectious and infectious agents with simultaneous detection of unusual patterns of disease occurrence in a target population. The subject technology can be used, among other purposes, to assist clinicians, emergency management personnel and administrators in tracking, detecting and reporting emerging illnesses as well as rarely occurring disease such as potential BTAs quickly and effectively, in order to improve responsiveness to and mitigation of the effects of a large-scale outbreak.

Real-time disease surveillance can be useful for early detection of emerging infectious diseases and/or the covert release of a biological threat agent.

In some implementations of the subject technology, computing device(s) are programmed to detect the spread of biological and infectious agents by analyzing symptoms as patients enter the emergency department (or another treatment facility). Some trend analysis systems look at data collected and analyzed in a batch and sent to a lab—sometimes up to two weeks after the patient is seen.

In some implementations of the subject technology, computing device(s) analyze the data in real-time, meaning the test results are entered into the system and analyzed without intentional delay, for example, within one minute, one hour, one day, or two days of the patient being seen. Using this technology, the computing device(s) can potentially identify an outbreak of influenza or even an Anthrax attack weeks in advance of some other systems—possibly saving valuable time in an emergency when even seconds matter.

The subject technology, in some examples, includes a real-time, scalable, extensible, automated, knowledge-based biological threat agent (BTA) detection and diagnosis system implemented on computing device(s). The subject technology, in some examples, conducts real-time analysis of multiple pre-diagnostic parameters from records already being collected within an emergency department (or other treatment facility), such as triage chief complaints, physician exam notes, and test orders and results.

The computing device(s), in some examples, can send alerts to physicians' pagers or mobile phones notifying the physicians of possible or confirmed cases of bioterrorism agents, for example, Anthrax, smallpox, or plague, when they are identified (e.g., within one minute of identification). The computing device(s) are able to map where those cases have appeared in the city, providing powerful pieces of information that could help physicians more quickly contain the outbreak.

Examples of the subject technology can be implemented with a Pre-Processor, an Inference Engine, an Alert Notification System, a Human Interaction System, a Memory Archiver and a set of relational databases managed by a Database Management System.

In some examples, the pre-processor receives messages (e.g., HL7 messages) sent to the computing device(s), removes any individually identifying information, and stores the HIPAA-compliant data in Experiential Memory. Each time new data is added to Experiential Memory, the inference engine sub-system determines whether or not this new information triggers a BTA alert. If the new data represents a confirmed case of a known BTA, then the inference engine can update the parameters of the associated model accordingly. BTA alerts can be triggered either by an individual case having a probability of diagnosis that is above a BTA-specific threshold, or by a group of similar cases—clustered in time or in space—that have a probability above a separate, and generally lower, BTA-specific threshold.

The subject technology, in some examples, can effectively balance the dual challenges of early detection of individual threat agents and simultaneous detection of unusual patterns of disease occurrence in a target population. Use of the subject technology can, among providing other benefits, assist clinicians in quickly and effectively detecting potential BTAs order to better respond to and mitigate the effects of a possible large-scale outbreak.

Figure 2:
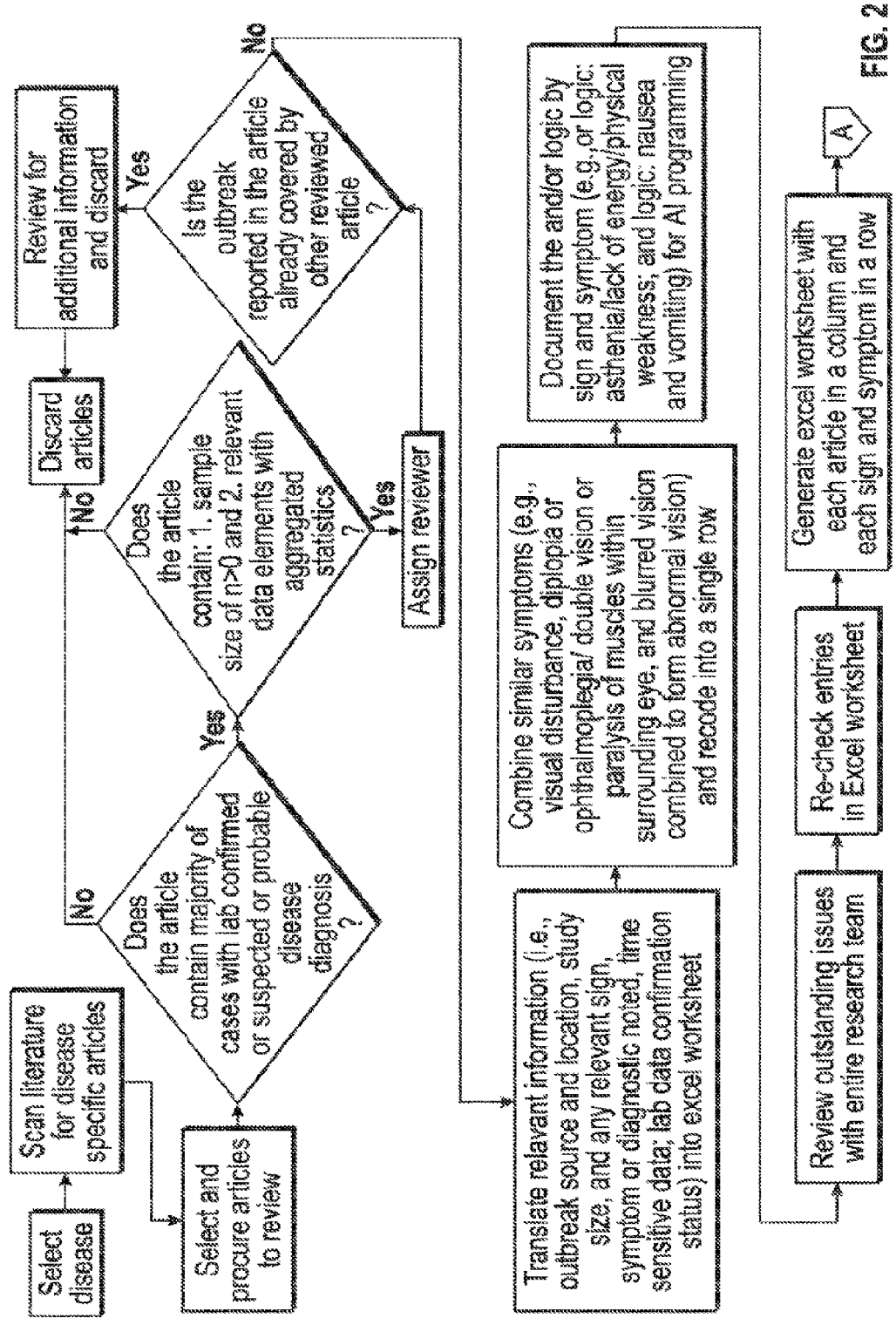
FIG. 2 illustrates an example profile development methodology based on literature.
Figure 3A:
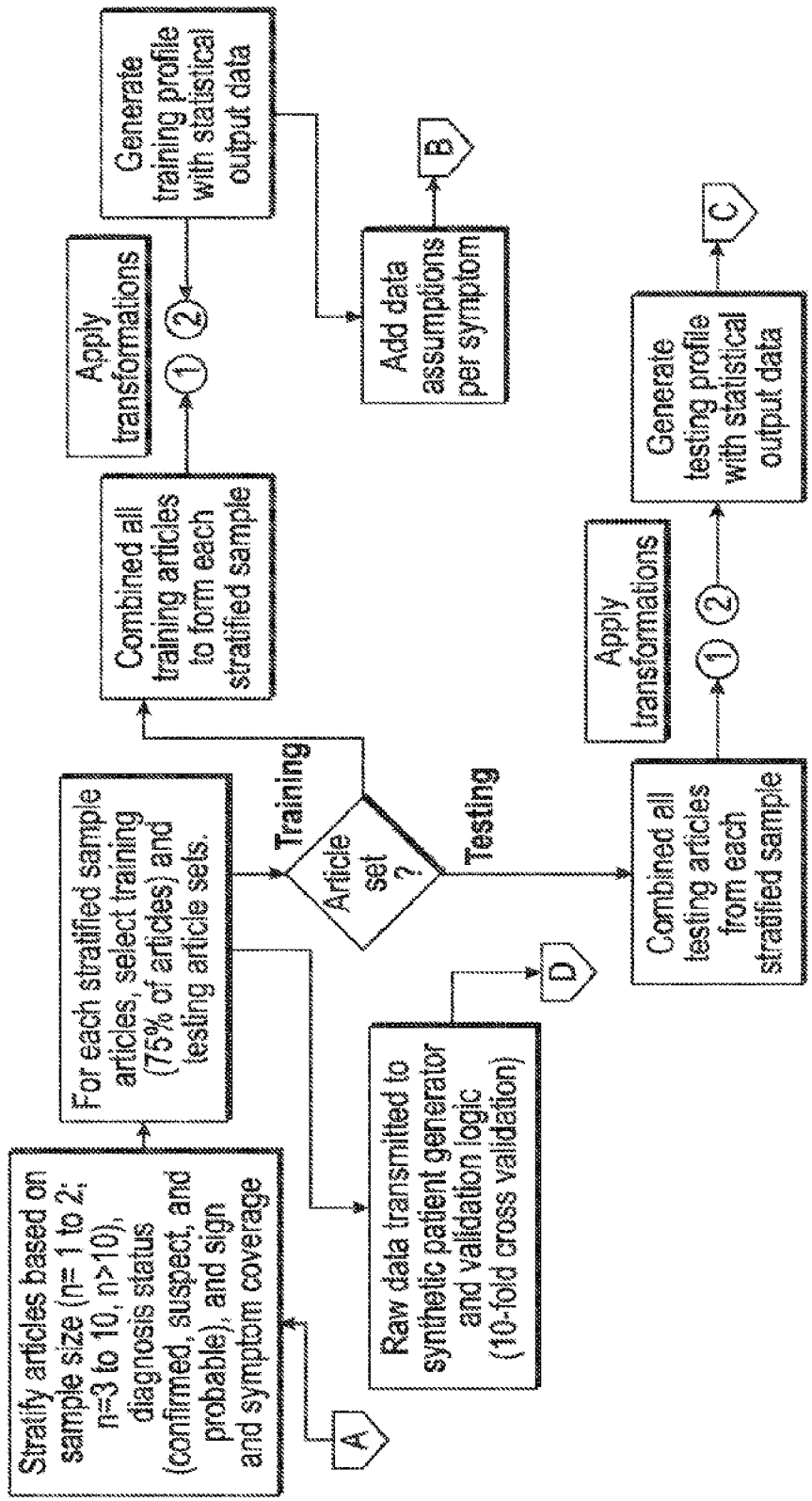
FIGS. 3A-3B illustrates an example profile development methodology based on data.
Figure 3B:
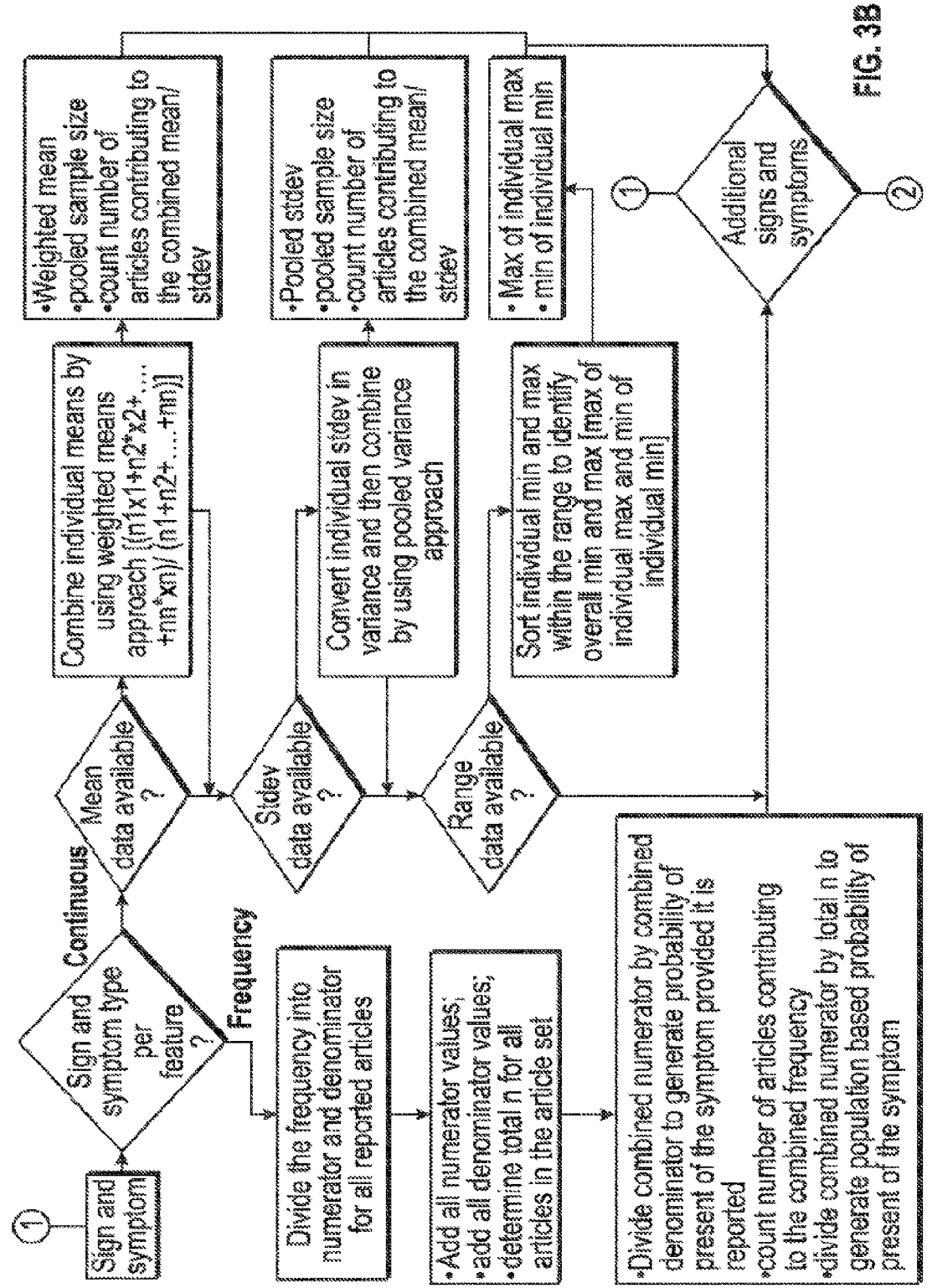
Figure 4:
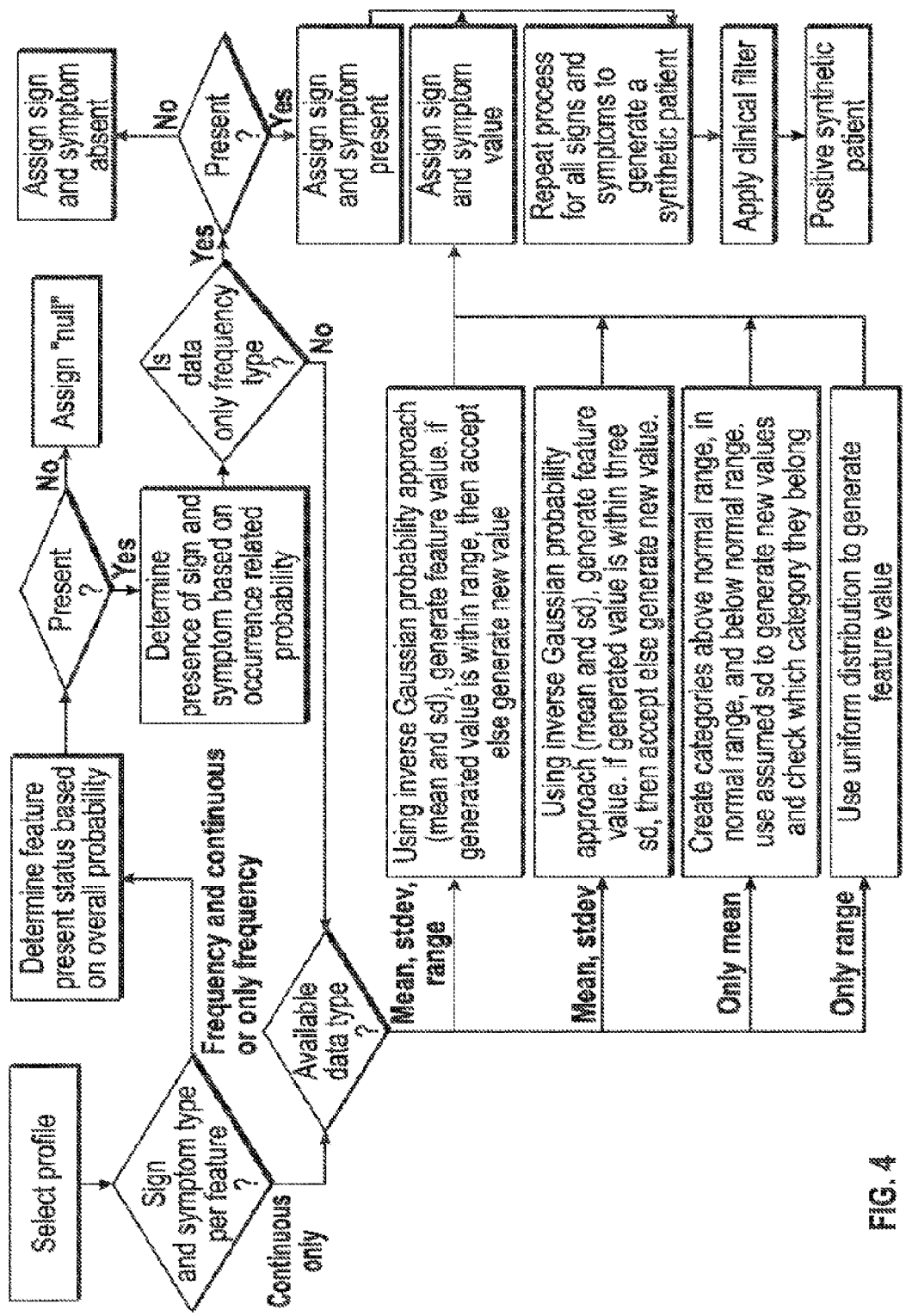
FIG. 4 illustrates an example synthetic patient generator logic.

FIG. 2 illustrates an example profile development methodology based on literature. FIGS. 3A-3B illustrates an example profile development methodology based on data. FIG. 4 illustrates an example synthetic patient generator logic.

Figure 5:
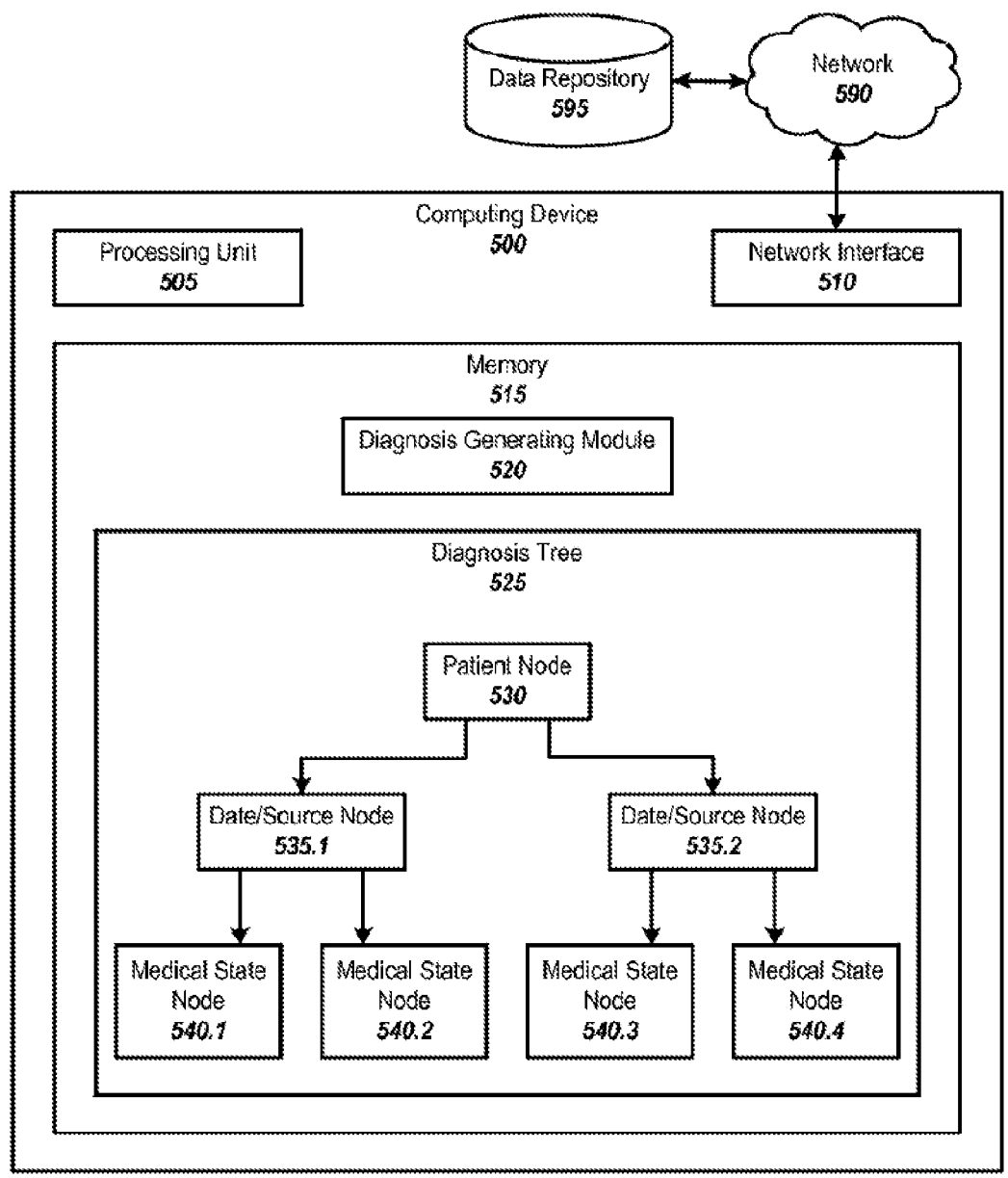
FIG. 5 illustrates an example computing device for generating a diagnosis for a patient.

FIG. 5 illustrates an example computing device 500 for generating a diagnosis for a patient. As shown, the computing device 500 includes a processing unit 505, a network interface 510, and a memory 515. The processing unit 505 includes one or more processors. The processing unit 505 may include a central processing unit (CPU), a graphics processing unit (GPU), or any other processing unit. The processing unit 505 executes computer instructions that are stored in a computer-readable medium, for example, the memory 515. The network interface 510 allows the computing device 500 to transmit and receive data in the network 590, which may include one or more of a local area network, a wide area network, a wired network, a wireless network, the Internet, a cellular network, etc. Using the network interface 510, the computing device 500 may communicate with remote computer(s) connected to the network 590, for example, a data repository 595. The memory 515 stores data and/or instructions. The memory 515 may be one or more of a cache unit, a storage unit, an internal memory unit, or an external memory unit. As illustrated, the memory 515 includes a diagnosis generating module 520 and a diagnosis tree 525.

The diagnosis generating module 520 may be implemented in software and may store instructions. The instructions, when executed, may cause the processing unit 505 to receive medical information for a patient. The medical information may be received via input device(s) (e.g., a keyboard or mouse) of the computing device 500 or via the network 590. The medical information may include multiple medical information items having different sources (e.g., medical records, physician assessments, test results, etc.). Each medical information item may include a date, a source, and a medical state. The medical state may be a symptom, a sign, a finding, or a test result. In some cases, the source is a test type (e.g., weight test) and the medical state is a test result (e.g., weighs 160 pounds). In some cases, the source is a medical record and the medical state is a fact noted in the medical record.

The diagnosis generating module 520 may include instructions which, when executed by the processing unit 505, cause the processing unit 505 to construct, in the memory 515 of the computing device 500, a diagnosis tree 525 for the patient. The diagnosis tree 525 includes a patient node 530. The children nodes of the patient node 530 are date/source nodes 535.1-2, which include a date and/or a source of medical information. The children of the date/source nodes 535.1-2 are medical state nodes 540.1-4, which include medical state information. While each parent node is illustrated as having two children nodes, in alternative implementations, each parent node may have any number of children nodes. Thus, there may be any number, not necessarily two, of date/source nodes 535, and any number, not necessarily four, of medical state nodes 540. Also, while a single diagnosis tree 525 for a single patient is illustrated, there may be multiple diagnosis trees for multiple patients.

The instructions in the diagnosis generating module 520, when executed, may cause the processing unit 505 to generate a diagnosis for the patient using the constructed diagnosis tree 525. In some examples, the processing unit 505 may compare the constructed diagnosis tree 525 to stored diagnostic information items for multiple diagnoses. The stored diagnostic information items may be stored in the data repository 595. The processing unit 505 may generate the diagnosis based on a similarity of the constructed diagnosis tree 525 to one or more of the stored diagnostic information items. The data repository 595 may be accessible to the computing device 500, including the processing unit 505, via the network 590.

Figure 6:
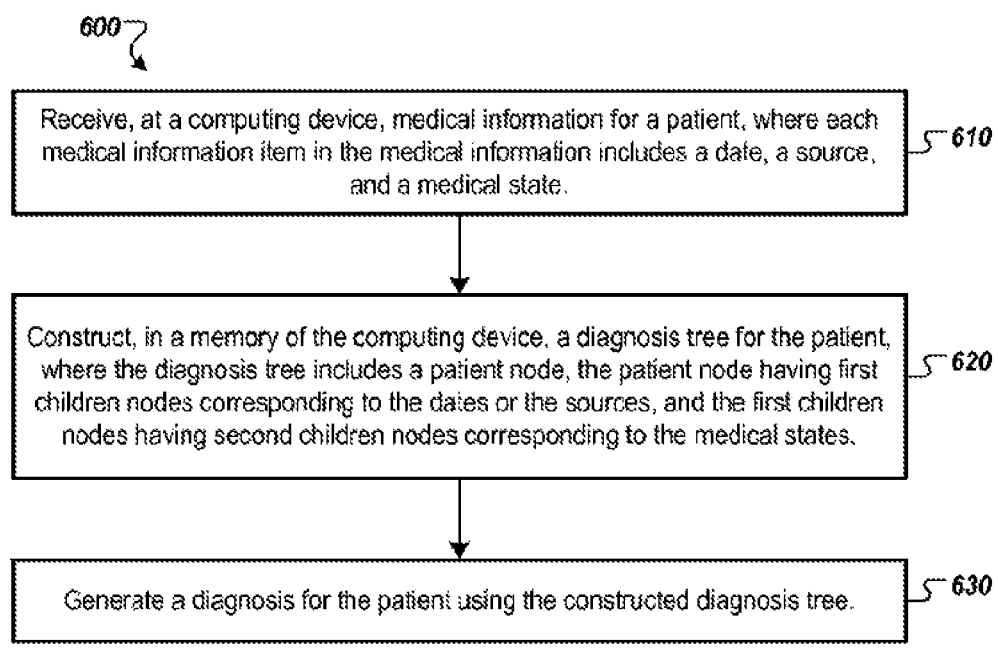
FIG. 6 illustrates an example process for generating a diagnosis for a patient.

FIG. 6 illustrates an example process 600 for generating a diagnosis for a patient. The process 600 begins at step 610, where a computing device (e.g., computing device 500) receives medical information for a patient. The medical information includes medical information items. Each medical information item includes a date, a source, and a medical state.

In step 620, the computing device constructs, in a memory (e.g., memory 515) of the computing device, a diagnosis tree for the patient. The diagnosis tree includes a patient node (e.g., patient node 530). The patient node has first children nodes (e.g., date/source nodes 535) corresponding to the dates or the sources. The first children nodes have second children nodes (e.g., medical state nodes 540) corresponding to the medical states. The date in the medical information and/or in the first children nodes may be a medical encounter date, and the sources may include free-form audio or text provided by a user. The medical information may include a fact determined based on the free-form audio or text.

In step 630, the computing device generates a diagnosis for the patient using the constructed diagnosis tree. The generated diagnosis may be provided to the patient or to a medical professional working with the patient via a display of the computing device or via a message (e.g., email, text message, or push notification to mobile device) generated at the computing device. After step 630, the process 600 ends.

Figure 7:
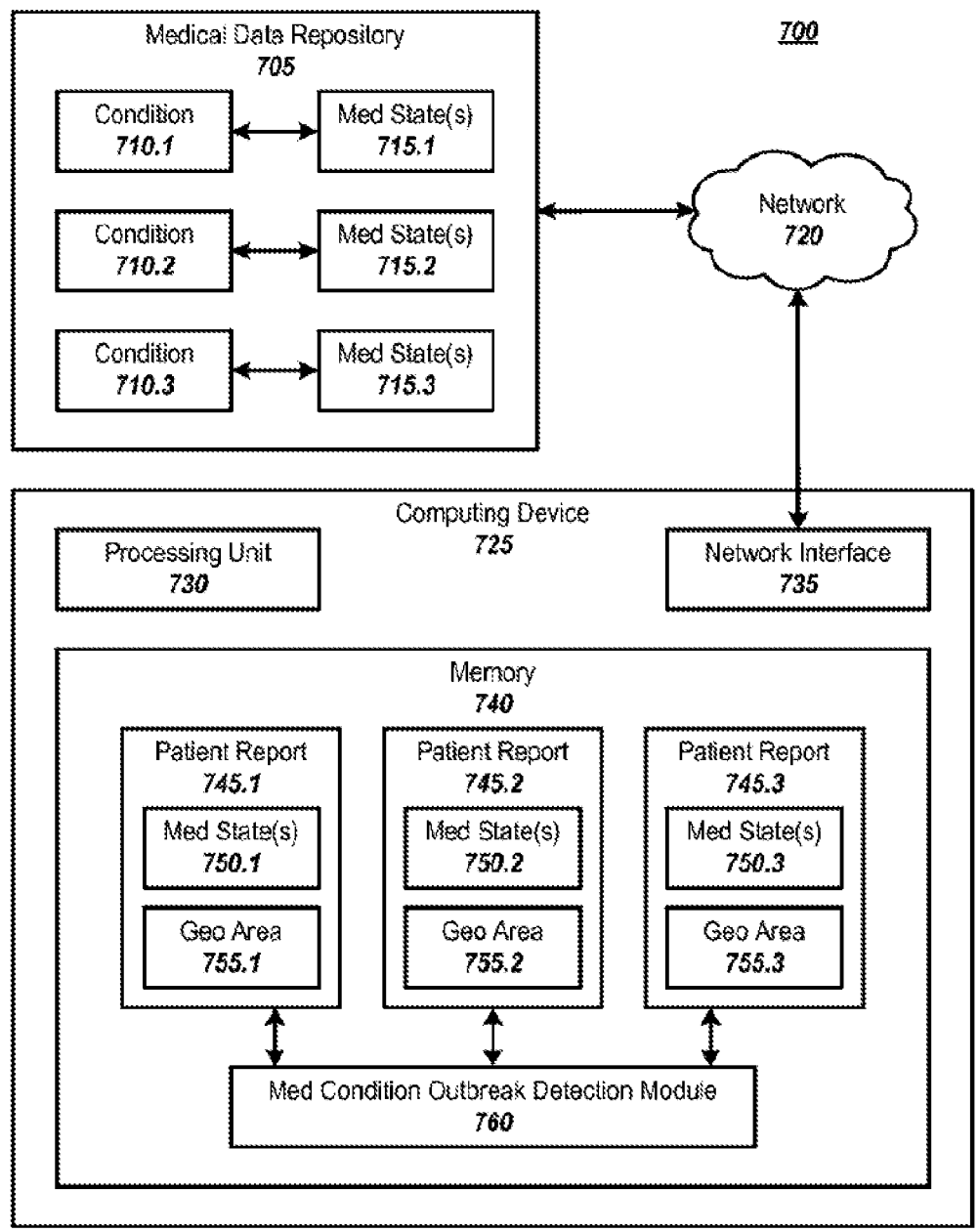
FIG. 7 illustrates an example system for determining an outbreak of a medical condition in a geographic area.

FIG. 7 illustrates an example system 700 for determining an outbreak of a medical condition in a geographic area. As shown, the system 700 includes a medical data repository 705 and a computing device 725 connected to one another via a network 720. The network 720 may include one or more of a local area network, a wide area network, a wired network, a wireless network, the Internet, a cellular network, etc.

As shown, the medical data repository 705 stores conditions 710.1-3. Each stored condition 710.$k$ is associated with medical state(s) 715.$k$, which may include expected measurement(s) or range(s) of symptom(s), sign(s), finding(s) or test result(s) for persons having the condition 710.$k$. Using the medical data repository 705, an input condition may be associated with output medical state(s) or input medical state(s) may be associated with an output condition. The medical data repository 705 may implement any data structure for associating condition(s) 710.1-3 with medical states 715.1-3, for example, a table, a hash table, a linked list, etc. Furthermore, the medical data repository 705 is shown as including three conditions 710.1-3 and associated medical states 715.1-3. However, the medical data repository 705 may store any number of conditions and associated medical states.

As shown, the computing device 725 includes a processing unit 730, a network interface 735, and a memory 740. The processing unit 730 includes one or more processors. The processing unit 730 may include a central processing unit (CPU), a graphics processing unit (GPU), or any other processing unit. The processing unit 730 executes computer instructions that are stored in a computer-readable medium, for example, the memory 740. The network interface 735 allows the computing device 725 to transmit and receive data in the network 720. Using the network interface 735, the computing device 725 may communicate with remote computer(s) connected to the network 720, for example, the medical data repository 705. The memory 740 stores data and/or instructions. The memory 740 may be one or more of a cache unit, a storage unit, an internal memory unit, or an external memory unit. As illustrated, the memory 740 includes patient reports 745.1-3 and a medical condition outbreak detection module 760.

The medical condition outbreak detection module 760 includes instructions which, when executed by the processing unit 730, cause the processing unit 730 to receive the patient reports 745.1-3. Each patient report 745.$k$ includes medical state(s) 750.$k$ and a geographic area 755.$k$. The medical state(s) may include symptom(s), sign(s), finding(s) or test result(s). The geographic area 755.$k$ may be a geographic area (e.g., a metropolitan area, for instance, the Los Angeles metropolitan area). The geographic area may correspond to a geographic area of a treatment facility generating the report (e.g., a treatment facility in the Los Angeles metropolitan area may be associated with Los Angeles) or the geographic area may correspond to a default (e.g., home or work) geographic area of the patient.

The exact home or work location of the patient may be obfuscated to protect the patient's privacy. For example, a patient report may indicate that a patient lives in the San Francisco metropolitan area, but may obfuscate that the patient's home address is 123 Main Street, Palo Alto, Calif. in order to protect the patient's privacy. In other words, the geographic area 755.$k$ may lack a geographic location, within the identified geographic area, associated with the patient. In some cases, exact home or work location(s) of patient(s) may not be obfuscated for accessing specific demographic information if permitted by the laws of the jurisdiction(s) in which the subject technology is implemented.

In some cases, each of the patient reports 745.1-3 is associated with the same geographic area. For example, all of the reports may be from the Los Angeles metropolitan area. As shown, there are three patient reports 745.1-3. However, the subject technology may be implemented with any number of patient reports 745.

The medical condition outbreak detection module 760 includes instructions which, when executed by the processing unit 730, cause the processing unit 730 to determine, based on data stored in the medical data repository 705, that the set of medical states 750 for at least a threshold number (e.g., 1000) of patient reports 745 in the same geographic area is associated with a specified condition (e.g., at least 1000 people in metropolitan Chicago have Anthrax). The processing unit 730 may use the associations of medical states 715.$k$ with conditions 710.$k$, stored in the medical data repository 705, to make this determination. The specified condition may be a diagnosable disease. Determining that the set of medical states is associated with the specified condition may include diagnosing, via the computing device 725, the patients associated with the patient reports as having the specified condition.

The medical condition outbreak detection module 760 includes instructions which, when executed by the processing unit 730, cause the processing unit 730 to determine an outbreak of the specified condition in the geographic area based on the reports of the at least the threshold number of patients having the set of medical states. The medical condition outbreak detection module 760 includes instructions which, when executed by the processing unit 730, cause the processing unit 730 to provide, to a user of the computing device 725, an indication of the outbreak of the specified condition.

Figure 8:
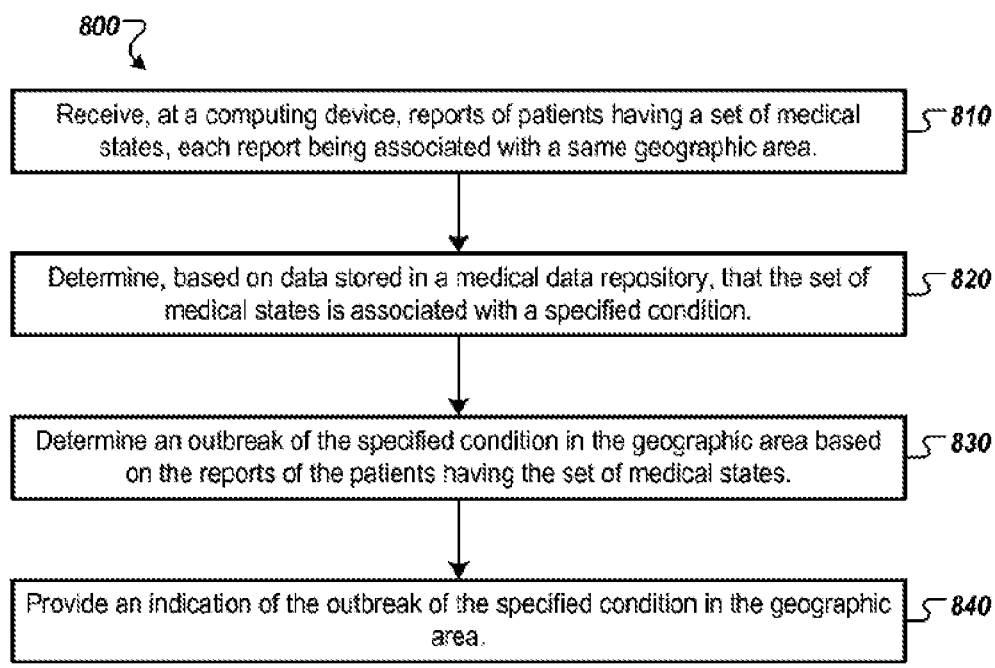
FIG. 8 illustrates an example process for determining an outbreak of a medical condition in a geographic area.

FIG. 8 illustrates an example process 800 for determining an outbreak of a medical condition in a geographic area. The process 800 begins at step 810, where a computing device (e.g., computing device 725) receives reports (e.g., patient reports 745) of patients having a set of medical conditions. Each report is associated with the same geographic area. The computing device may also receive other reports associated with different geographic areas. The computing device may receive the reports from various treatment facilities (e.g., hospitals, clinics, doctors' offices) over a network (e.g., network 720) using a secure and encrypted network communication technology.

In step 820, the computing device determines, based on data stored in a medical repository (e.g., medical data repository 705), that the set of medical states in the reports is associated with a specified condition. For example, the computing device may determine that at least a threshold number (e.g., 2000) of reports correspond to patients in the State of Rhode Island suffering from polio.

In step 830, the computing device determines an outbreak of the specified condition (e.g., polio) in the geographic area (e.g., Rhode Island) based on the reports of the patients having the set of medical states. If a large number (e.g., a number exceeding a threshold) of patients in a geographic area have a rare condition, there is likely an outbreak of the condition in the geographic area In step 840, the computing device provides an indication of the outbreak of the specified condition in the geographic area. The indication of the outbreak may be provided via a display unit of the computing device or via an electronic message (e.g., email, text message or push notification to a mobile device) transmitted from the computing device to a predetermined messaging address or message-receiving device.

As a result of some implementations of the subject technology, a disease outbreak in a geographic area may be detected more quickly and more efficiently and, thus, responded to more quickly and more efficiently. The response to the disease outbreak may include, for example, provision of medical supplies for treatment. After step 840, the process 800 ends.

Figure 9:
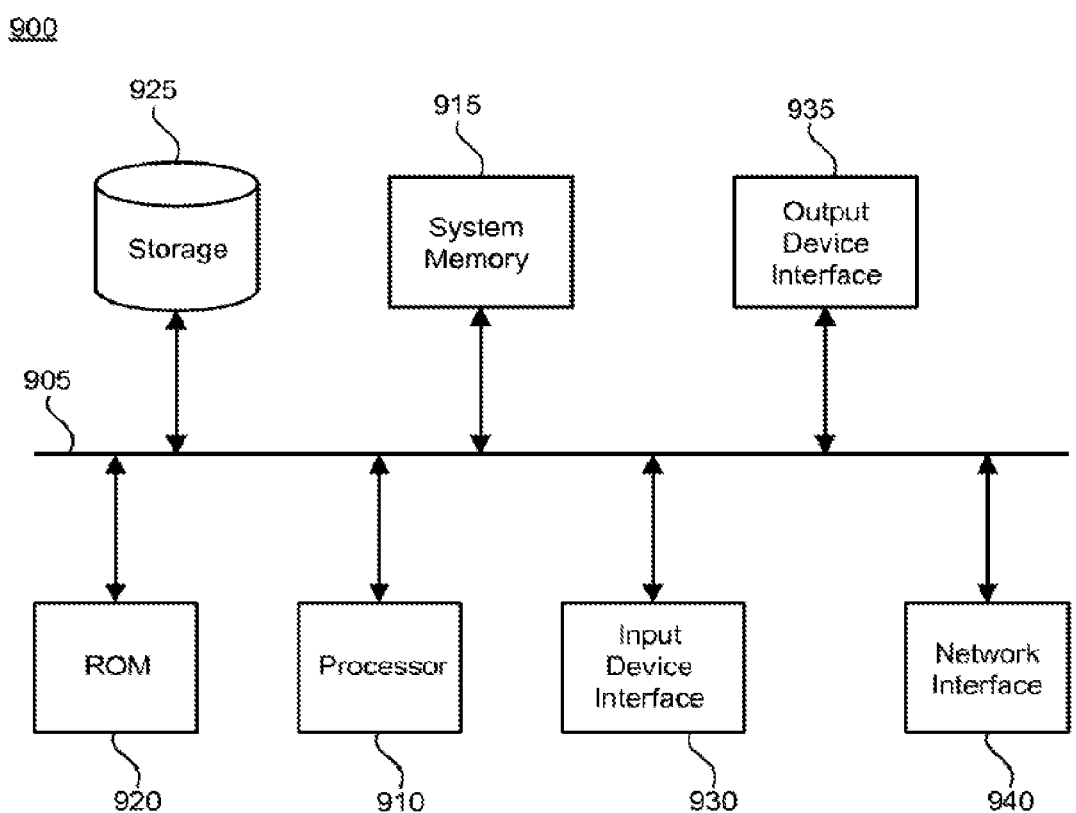
FIG. 9 conceptually illustrates an example electronic system with which some implementations of the subject technology are implemented.

FIG. 9 conceptually illustrates an electronic system 900 with which some implementations of the subject technology are implemented. For example, one or more of the data repository 595, the medical data repository 705, or the computing devices 500 and 725 may be implemented using the arrangement of the electronic system 900. The electronic system 900 can be a computer (e.g., a mobile phone, PDA), or any other sort of electronic device. Such an electronic system includes various types of computer readable media and interfaces for various other types of computer readable media. Electronic system 900 includes a bus 905, processing unit(s) 910, a system memory 915, a read-only memory 920, a permanent storage device 925, an input device interface 930, an output device interface 935, and a network interface 940.

The bus 905 collectively represents all system, peripheral, and chipset buses that communicatively connect the numerous internal devices of the electronic system 900. For instance, the bus 905 communicatively connects the processing unit(s) 910 with the read-only memory 920, the system memory 915, and the permanent storage device 925.

From these various memory units, the processing unit(s) 910 retrieves instructions to execute and data to process in order to execute the processes of the subject technology. The processing unit(s) can be a single processor or a multi-core processor in different implementations.

The read-only-memory (ROM) 920 stores static data and instructions that are needed by the processing unit(s) 910 and other modules of the electronic system. The permanent storage device 925, on the other hand, is a read-and-write memory device. This device is a non-volatile memory unit that stores instructions and data even when the electronic system 900 is off. Some implementations of the subject technology use a mass-storage device (for example a magnetic or optical disk and its corresponding disk drive) as the permanent storage device 925.

Other implementations use a removable storage device (for example a floppy disk, flash drive, and its corresponding disk drive) as the permanent storage device 925. Like the permanent storage device 925, the system memory 915 is a read-and-write memory device. However, unlike storage device 925, the system memory 915 is a volatile read-and-write memory, such a random access memory. The system memory 915 stores some of the instructions and data that the processor needs at runtime. In some implementations, the processes of the subject technology are stored in the system memory 915, the permanent storage device 925, or the read-only memory 920. For example, the various memory units include instructions for generating a diagnosis or detecting an outbreak of a medical condition in accordance with some implementations. From these various memory units, the processing unit(s) 910 retrieves instructions to execute and data to process in order to execute the processes of some implementations.

The bus 905 also connects to the input and output device interfaces 930 and 935. The input device interface 930 enables the user to communicate information and select commands to the electronic system. Input devices used with input device interface 930 include, for example, alphanumeric keyboards and pointing devices (also called "cursor control devices"). Output device interfaces 935 enables, for example, the display of images generated by the electronic system 900. Output devices used with output device interface 935 include, for example, printers and display devices, for example cathode ray tubes (CRT) or liquid crystal displays (LCD). Some implementations include devices for example a touch screen that functions as both input and output devices.

Finally, as shown in FIG. 9, bus 905 also couples electronic system 900 to a network (not shown) through a network interface 940. In this manner, the electronic system 900 can be a part of a network of computers (for example a local area network (LAN), a wide area network (WAN), or an Intranet, or a network of networks, for example the Internet. Any or all components of electronic system 900 can be used in conjunction with the subject technology.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage or flash storage, for example, a solid-state drive, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, for example is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some aspects of the disclosed subject matter, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, an "aspect" does not imply that the aspect is essential to the subject technology or that the aspect applies to all configurations of the subject technology. A disclosure relating to an aspect may apply to all configurations, or one or more configurations. A phrase, for example, an aspect may refer to one or more aspects and vice versa. A phrase, for example, a "configuration" does not imply that such configuration is essential to the subject technology or that such configuration applies to all configurations of the subject technology. A disclosure relating to a configuration may apply to all configurations, or one or more configurations. A phrase, for example, a configuration may refer to one or more configurations and vice versa.

What is claimed is:

1. A method comprising:

receiving, via one or more network ports of a first computing device, a plurality of medical information messages indicating medical state information for a plurality of patients;

generating, in real-time and without user interaction, a plurality of non-identifying patient reports based on removing individually-identifying patient information from the received medical information messages and converting respective address information for each of the received medical information messages to respective geographical areas that do not identify a patient address, wherein each non-identifying patient report includes medical state information for a respective patient;

constructing, a diagnosis tree for each of the plurality of patients, the diagnosis tree comprising a patient node comprising at least one node, wherein the at least one node corresponding to at least one item in the medical state information;

diagnosing, based on the constructed diagnosis tree, at least one patient having a specified condition;

determining, in real-time and without user interaction, whether a number of the at least one patient having the specified condition for a geographic area exceeds a threshold; and when it is determined that the number of the at least one patient having the specified condition for the geographic area exceeds the threshold:
  determining an outbreak of the specified condition for the geographic area, wherein the geographic area comprises a metropolitan area,
  providing, in real-time to a user interface for display at a second computing device remote from the first computing device, an indication of the outbreak of the specified condition and the geographic area, and
  providing, to the user interface and based on the provided indication, a response package comprising clinical procedures associated with the specified condition.

2. The method of claim 1, wherein the medical state information comprises a set of symptoms, signs, findings, or test results,
  wherein the specified condition comprises a diagnosable disease, and
  wherein the diagnosing the at least one patient having the specified condition comprises diagnosing the at least one patient associated with a corresponding non-identifying patient report as having the diagnosable disease based on the set of symptoms, signs, findings, or test results.

3. The method of claim 1, wherein:
  the metropolitan area corresponds to a geographic location of treatment facilities generating the non-identifying patient reports, or corresponds to a default geographic location of patients associated with the non-identifying patient reports; and
  a default geographic location of each patient is obfuscated.

4. The method of claim 1, wherein the respective address information is converted to geographic coordinates within the respective geographic areas, associated with a corresponding patient.

5. The method of claim 1, wherein providing the indication of the outbreak comprises transmitting an electronic message to a mobile device.

6. A non-transitory computer-readable medium comprising instructions which, when executed by one or more computers, cause the one or more computers to:
  receive a plurality of medical information messages indicating medical state information for a plurality of patients;
  generate, in real-time and without user interaction, a plurality of non-identifying patient reports based on removing individually-identifying patient information from the received medical information messages and converting respective address information for each of the received medical information messages to respective geographical areas that do not identify a patient address, wherein each non-identifying patient report includes medical state information for a respective patient;
  construct, a diagnosis tree for each of the plurality of patients, the diagnosis tree comprising a patient node comprising at least one node, wherein the at least one node corresponding to at least one item in the medical state information;
  diagnose, based on the constructed diagnosis tree, at least one patient having a specified condition;
  determine, in real-time and without user interaction, whether a number of the at least one patient having the specified condition for a geographic area exceeds a threshold; and when it is determined that the number of the at least one patient having the specified condition for the geographic area exceeds the threshold:
  determine an outbreak of the specified condition for the geographic area, wherein the geographic area comprises a metropolitan area,
  provide, in real-time to a user interface for display at a remote computing device, an indication of the outbreak of the specified condition and the geographic area, and
  provide, to the user interface and based on the provided indication, a response package comprising clinical procedures associated with the specified condition.

7. The computer-readable medium of claim 6, wherein the medical state information comprises a set of symptoms, signs, findings, or test results, and
  wherein the specified condition comprises a diagnosable disease.

8. The computer-readable medium of claim 7, wherein the instructions to diagnose the at least one patient having the specified condition comprises instructions which, when executed by the one or more computers, cause the one or more computers to diagnose the at least one patient associated with a corresponding non-identifying patient report as having the diagnosable disease based on the set of symptoms, signs, findings, or test results.

9. The computer-readable medium of claim 6, wherein:
  the metropolitan area corresponds to a geographic location of treatment facilities generating the non-identifying patient reports, or corresponds to a default geographic location of patients associated with the non-identifying patient reports; and
  a default geographic location of each patient is obfuscated.

10. The computer-readable medium of claim 6, wherein the respective address information is converted to geographic coordinates within the respective geographic areas, associated with a corresponding patient.

11. The computer-readable medium of claim 6, wherein the instructions to provide the indication of the outbreak comprise instructions which, when executed by the one or more computers, transmit an electronic message to a mobile device.

12. A system comprising:
  one or more computing devices; and
  a memory comprising instructions which, when executed by one or more computing devices, cause the one or more computing devices to:
    receive a plurality of medical information messages indicating medical state information for a plurality of patients;
    generate, in real-time and without user interaction, a plurality of non-identifying patient reports based on removing individually-identifying patient information from the received medical information messages and converting respective address information for each of the received medical information messages to respective geographical areas that do not identify a patient address, wherein each non-identifying patient report includes medical state information for a respective patient;
    construct, a diagnosis tree for each of the plurality of patients, the diagnosis tree comprising a patient node comprising at least one node, wherein the at least one node corresponding to at least one item in the medical state information;

diagnose, based on the constructed diagnosis tree, at least one patient having a specified condition;

determine, in real-time and without user interaction, whether a number of the at least one patient having the specified condition for a geographic area exceeds a threshold; and when it is determined that the number of the at least one patient having the specified condition for the geographic area exceeds the threshold:

determine an outbreak of the specified condition for the geographic area, wherein the geographic area comprises a metropolitan area, provide, in real-time to a user interface for display at a remote computing device, an indication of the outbreak of the specified condition and the geographic area, and provide, to the user interface and based on providing the indication, a response package comprising clinical procedures associated with the specified condition.

13. The system of claim 12, wherein the medical state information comprises a set of symptoms, signs, findings, or test results.

14. The system of claim 13, wherein the instructions to diagnose the at least one patient having the specified condition comprises instructions which, when executed by the one or more computing devices, cause the one or more computing devices to diagnose the at least one patient associated with a corresponding non-identifying patient report as having the specified condition based on the set of symptoms, signs, findings, or test results.

15. The system of claim 12, wherein:

the metropolitan area corresponds to a geographic location of treatment facilities generating the non-identifying patient reports, or corresponds to a default geographic location of patients associated with the non-identifying patient reports; and a default geographic location of each patient is obfuscated.

16. The system of claim 12, wherein the respective address information is converted to geographic coordinates within the respective geographic areas, associated with a corresponding patient.

17. The system of claim 12, wherein the instructions to provide the indication of the outbreak comprise instructions which, when executed by the one or more computing devices, transmit an electronic message to a mobile device.

* * * * *